(12) United States Patent
Eckman (10) Patent No.: US 8,167,886 B2
(45) Date of Patent: May 1, 2012

(54) INSERTION TOOL FOR A VERTEBRAL DEFECT DEVICE

(75) Inventor: Walter W. Eckman, Tupelo, MS (US)

(73) Assignee: Concept Matrix, LLC, Orlando, FL (US)

( * ) Notice: Subject to any disclaimer, the term of this patent is extended or adjusted under 35 U.S.C. 154(b) by 220 days.

(21) Appl. No.: 12/643,693

(22) Filed: Dec. 21, 2009

(65) Prior Publication Data

US 2010/0100140 A1   Apr. 22, 2010

Related U.S. Application Data

(60) Division of application No. 11/463,056, filed on Aug. 8, 2006, now Pat. No. 7,674,295, which is a continuation-in-part of application No. 10/988,830, filed on Nov. 15, 2004, now Pat. No. 7,534,267, which is a division of application No. 10/345,591, filed on Jan. 16, 2003, now Pat. No. 7,105,023.

(60) Provisional application No. 60/349,730, filed on Jan. 17, 2002, provisional application No. 60/369,510, filed on Apr. 2, 2002.

(51) Int. Cl.
*A61B 17/56* (2006.01)
*A61F 2/44* (2006.01)

(52) U.S. Cl. ............ 606/86 A; 606/246; 623/17.11

(58) Field of Classification Search ............ None
See application file for complete search history.

(56) References Cited

U.S. PATENT DOCUMENTS

| | | |
|---|---|---|
| 4,349,921 A | 9/1982 | Kuntz |
| 4,545,374 A | 10/1985 | Jacobson |
| 4,936,848 A | 6/1990 | Bagby |
| 4,961,740 A | 10/1990 | Ray et al. |
| 5,258,031 A | 11/1993 | Salib et al. |
| D356,129 S | 3/1995 | Wolf |
| 5,425,773 A | 6/1995 | Boyd et al. |
| 5,484,437 A | 1/1996 | Michelson |
| 5,522,899 A | 6/1996 | Michelson |
| 5,549,679 A | 8/1996 | Kuslich |
| 5,562,738 A | 10/1996 | Boyd et al. |
| 5,571,189 A | 11/1996 | Kuslich |

(Continued)

FOREIGN PATENT DOCUMENTS

EP   1099429 A1   5/2001

(Continued)

OTHER PUBLICATIONS

Office Action Issued May 25, 2010 in EP Application No. 03731980.3.

(Continued)

*Primary Examiner* — David H Willse
*Assistant Examiner* — Javier Blanco
(74) *Attorney, Agent, or Firm* — Panitch Schwarze Belisario & Nadel LLP (57) ABSTRACT

An insertion tool for a vertebral defect device having upper and lower openings includes a first finger sized and shaped to cooperatively engage the upper opening. A second finger is sized and shaped to cooperatively engage the lower opening. An outer surface of each finger is shaped to match a contoured shape of the vertebral defect device proximate to the respective finger to allow a smooth insertion of the vertebral defect device between a pair of adjacent vertebrae. A driving member is sized and shaped to engage a body of the vertebral defect device, such that during insertion the driving member is driven to push the vertebral defect device between the pair of adjacent vertebrae.

6 Claims, 9 Drawing Sheets

U.S. PATENT DOCUMENTS

| | | |
|---|---|---|
| D377,095 S | 12/1996 | Michelson |
| D377,096 S | 12/1996 | Michelson |
| D377,527 S | 1/1997 | Michelson |
| 5,593,409 A | 1/1997 | Michelson |
| 5,609,635 A | 3/1997 | Michelson |
| 5,609,636 A | 3/1997 | Kohrs et al. |
| 5,645,596 A | 7/1997 | Kim et al. |
| 5,653,761 A | 8/1997 | Pisharodi |
| 5,669,909 A | 9/1997 | Zdeblick et al. |
| 5,674,296 A | 10/1997 | Bryan et al. |
| 5,702,449 A | 12/1997 | McKay |
| 5,766,252 A | 6/1998 | Henry et al. |
| 5,776,199 A | 7/1998 | Michelson |
| 5,785,710 A | 7/1998 | Michelson |
| 5,888,226 A | 3/1999 | Rogozinski |
| 5,906,616 A | 5/1999 | Pavlov et al. |
| 5,980,522 A | 11/1999 | Koros et al. |
| 5,984,967 A | 11/1999 | Zdeblick et al. |
| 6,039,762 A | 3/2000 | McKay |
| D425,989 S | 5/2000 | Michelson |
| 6,102,950 A | 8/2000 | Vaccaro |
| 6,113,637 A | 9/2000 | Gill et al. |
| 6,136,031 A | 10/2000 | Middleton |
| 6,174,334 B1 | 1/2001 | Suddaby |
| 6,193,757 B1 | 2/2001 | Foley et al. |
| 6,210,412 B1 | 4/2001 | Michelson |
| 6,245,108 B1 | 6/2001 | Biscup |
| 6,270,528 B1 | 8/2001 | McKay |
| 6,309,421 B1 | 10/2001 | Pisharodi |
| 6,419,705 B1 | 7/2002 | Erickson |
| 6,425,920 B1 | 7/2002 | Hamada |
| 6,447,544 B1 | 9/2002 | Michelson |
| 6,447,547 B1 | 9/2002 | Michelson |
| 6,454,805 B1 | 9/2002 | Baccelli et al. |
| 6,468,311 B2 | 10/2002 | Boyd et al. |
| 6,478,822 B1 | 11/2002 | Leroux et al. |
| 6,478,823 B1 | 11/2002 | Michelson |
| 6,520,991 B2 | 2/2003 | Huene |
| 6,558,424 B2 | 5/2003 | Thalgott |
| 6,582,433 B2 | 6/2003 | Yun |
| 6,607,558 B2 | 8/2003 | Kuras |
| 6,648,917 B2 | 11/2003 | Gerbec et al. |
| 6,824,564 B2 | 11/2004 | Crozet |
| 6,852,129 B2 | 2/2005 | Gerbec et al. |
| 6,855,168 B2 | 2/2005 | Crozet |
| 6,902,581 B2 | 6/2005 | Walkenhorst et al. |
| 6,923,810 B1 | 8/2005 | Michelson |
| 7,011,684 B2 | 3/2006 | Eckman |
| 7,046,714 B2 | 5/2006 | Nicolaescu et al. |
| 7,112,222 B2 | 9/2006 | Fraser et al. |
| 7,125,425 B2 | 10/2006 | Foley et al. |
| 7,156,877 B2 | 1/2007 | Lotz et al. |
| 7,163,561 B2 | 1/2007 | Michelson |
| 7,503,933 B2 | 3/2009 | Michelson |
| 2001/0018614 A1 | 8/2001 | Bianchi |
| 2002/0116009 A1 | 8/2002 | Fraser et al. |
| 2003/0004576 A1 | 1/2003 | Thalgott |
| 2004/0054412 A1 | 3/2004 | Gerbec et al. |
| 2004/0254644 A1 | 12/2004 | Taylor |
| 2005/0004672 A1 | 1/2005 | Pafford et al. |
| 2005/0159816 A1 | 7/2005 | Walkenhorst et al. |
| 2008/0015581 A1 | 1/2008 | Eckman |
| 2008/0015695 A1 | 1/2008 | Eckman |

FOREIGN PATENT DOCUMENTS

| | | |
|---|---|---|
| EP | 1112753 A1 | 7/2001 |
| FR | 2742044 A1 | 6/1997 |
| FR | 2762779 A1 | 11/1998 |
| FR | 2794967 A1 | 12/2000 |
| GB | 2097594 A | 11/1982 |
| WO | 9640014 A1 | 12/1996 |
| WO | 9714377 A1 | 4/1997 |
| WO | 9932054 A1 | 7/1999 |

OTHER PUBLICATIONS

Office Action Issued Sep. 2, 2010 in U.S. Appl. No. 12/141,702.
Office Action dated Jul. 23, 2009, in related U.S. Appl. No. 11/741,200.
Office Action dated May 29, 2009, in related U.S. Appl. No. 11/741,200.
Depraetere, P., et al., Interbody Cages in PLIF Surgery: A Multicentric Report, Journal of Musculoskeletal Research, vol. 2, No. 1 (1998) 9-14.
Helmut D. Link et al., "Link SB Charite Artificial Disc: History, Design & Biomechanics", Spinal Restabilization Proceddures, Edited by D.L. Kaech and J.R. Jinkins, 297-298 (2002), Berlin, Germany.
Paul C. McAfee, Artificial Disc Prosthesis: The Link SB Charite IIIa, Spinal Restabilization Procedures, edited by D.L. Kaech and J.R. Jinkins, 299-301 (202) Towson, MD.
"Prodisc" Brochure, Spine Soutions, New York, NY.
"Link SB Charitea Artificial Disc" Brochure, Maintaining Natural Mobility, Link Spine Group, Branford, Connecticut.
"Prodisc" Brochure, Spine Solutions: The Non-Fusion Technology Company.
"Spine Arthroplasty", Spine Industry Analysis Series, Viscogliosi Bros., LLC, Nov. 2001.
Office Action dated Jan. 26, 2005, in related U.S. Appl. No. 10/345,591.
Office Action dated Nov. 30, 2005, in related U.S. Appl. No. 10/345,591.
Office Action dated Jul. 2, 2008, in related U.S. Appl. No. 10/988,830.
Supplementary European Search Report dated Feb. 18, 2008, in European Paten Application No. 03731980.3.
Int'l Search Report dated Jun. 30, 2003, in related PCT/US03/01508.
Office Action dated Jan. 27, 2009, in related European Patent Application No. 03731980.3.

INSERTION TOOL FOR A VERTEBRAL DEFECT DEVICE

CROSS-REFERENCE TO RELATED APPLICATIONS

The present application is a divisional of co-pending U.S. patent application Ser. No. 11/463,056, filed Aug. 8, 2006 and entitled "Vertebral Defect Device," which is a is a continuation-in-part of U.S. patent application Ser. No. 10/988,830, filed Nov. 15, 2004 and entitled "Methods of Installing a Vertebral Defect Device," now U.S. Pat. No. 7,534,267, which is a divisional of U.S. patent application Ser. No. 10/345,591, filed Jan. 16, 2003 and entitled "Vertebral Defect Device," now U.S. Pat. No. 7,105,023. This application claims benefit of U.S. Provisional Patent Application No. 60/369,510, filed Apr. 2, 2002 and entitled "Intervetebral Fusion Cage," and U.S. Provisional Patent Application No. 60/349,730, filed Jan. 17, 2002 and entitled "Intervetebral Fusion Cage."

BACKGROUND OF THE INVENTION

The present invention relates generally to intervertebral defect devices, and more particularly, to an insertion tool for inserting an intervertebral defect device into an intervertebral space using minimally invasive techniques.

Figure 9:
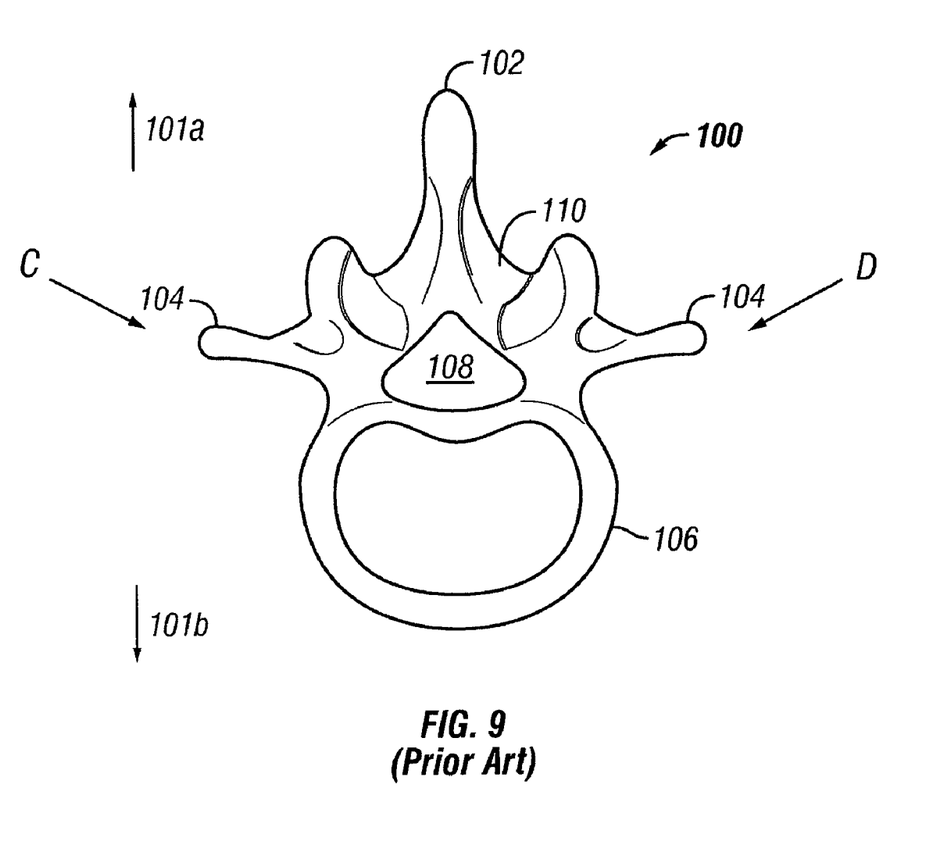
FIG. 9 is a top sectional view of a human vertebra as is known in the art.
Figure 10:
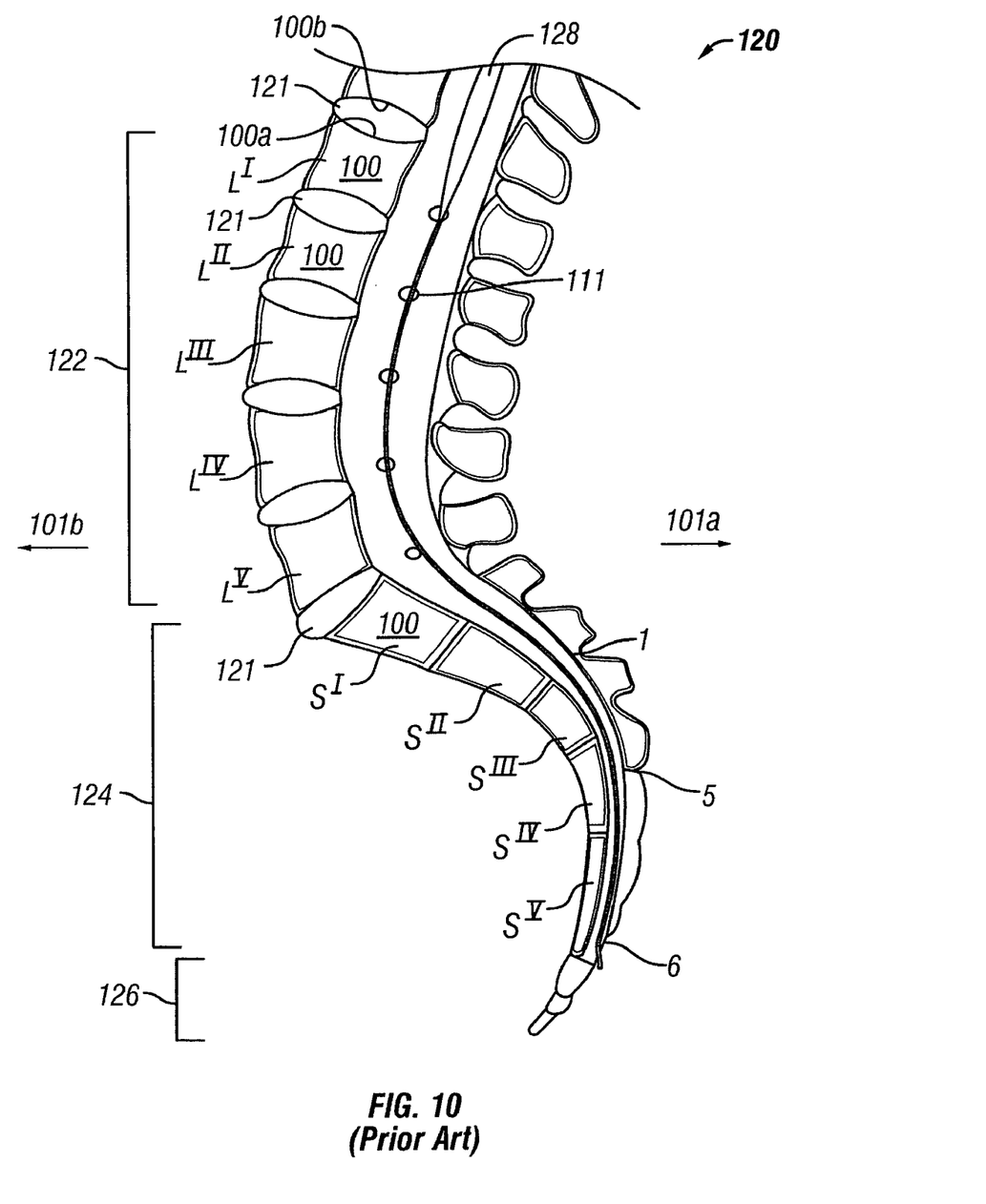
FIG. 10 is a side sectional view of a portion of a human spine as is known in the art.

Referring to prior art FIGS. 9 and 10, the spine 120, also known as the vertebral column or the spinal column, is a flexible column of vertebrae 100 (special types of bones) held together by muscles, ligaments and tendons. The spine 120 extends from the cranium (not shown) to the coccyx 126, encasing a spinal cord 128 and forming the supporting axis of the body (not shown). The spinal cord 128 is a thick bundle of nerve tissue (nerves) that branch off to various areas of the body for the purposes of motor control, sensation, and the like. The spine 120 includes seven cervical vertebrae (not shown), twelve thoracic vertebrae (not shown), five lumbar vertebrae, $L^I$-$L^V$, five sacral vertebrae, $S^I$-$S^V$, and three coccyx vertebrae 126. The sacral and coccyx vertebrae are each fused, thereby functioning as a single unit. FIG. 10 shows the lumbar region 122, the sacral region 124 and the coccyx 126 of the spine 120 and that the vertebrae 100 are stacked one upon another. The top portion 100a and bottom portion 100b of each vertebrae 100 is slightly concave. The opposing concave vertebral surfaces form the intervertebral space 121 in which an intervertebral disk (not shown) resides. Each of the intervertebral disks has a soft core referred to as a nucleus pulposus or nucleus (not shown).

In FIG. 9, directional arrow 101a is pointing in the posterior direction and directional arrow 101b is pointing in the anterior direction. FIG. 9 shows that each vertebrae 100 includes a body 106 in the innermost portion, a spinal canal 108 and a spinous process 102 at the posterior-most end of the vertebra 100. The vertebrae 100 are substantially similar in composition, but vary in size from the larger lumbar vertebrae to the smallest coccyx vertebrae 126. Each vertebrae 100 further includes two transverse processes 104 located on either side and a protective plate-like structure referred to as a lamina 110. Nerves from the spinal cord 128 pass through the spinal canal 108 and foramina 111 to reach their respective destinations within the body.

The natural aging process can cause a deterioration of the intervertebral disks, and therefore, their intrinsic support strength and stability is diminished. Sudden movements may cause a disk to rupture or herniate. A herniation of the disk is primarily a problem when the nucleus pulposus protrudes or ruptures into the spinal canal 108 placing pressure on nerves which in turn causes spasms, tingling, numbness, and/or pain in one or more parts of the body, depending on the nerves involved. Further deterioration of the disk can cause the damaged disk to lose height and as bone spurs develop on the vertebrae 100, result in a narrowing of the spinal canal 108 and foramen 111 (not shown clearly), and thereby causes pressure on the nerves emanating from the spinal cord 128.

Presently, there are several techniques, in addition to non-surgical treatments, for relieving the symptoms related to intervertebral disk deterioration. Surgical options include chemonucleolysis, laminectomy, diskectomy, microdiskectomy, and spinal fusion.

Chemonucleolysis is the injection of an enzyme, such as chymopapain, into the disk to dissolve the protruding nucleus pulposus. The enzyme is a protein-digesting enzyme and is used to dissolve the disk material. Since the enzyme is essentially a tissue-dissolving agent, it is indiscriminate in the protein-based matter it dissolves. Should the enzyme be injected into the wrong place, or if there is a breach in the disk capsule that would allow the solution to enter the spinal canal or to contact nerve tissue or the like, the resultant damage to nerve tissue could not be reversed. Even worse, about half of the patients who receive chemonucleolysis treatments experience increased back pain and muscle spasms immediately after the injection and more than half have incapacitating back pain for durations up to three months after such treatments.

A laminectomy is performed to decompress the spinal canal by open surgical techniques under general anesthesia. In this procedure, the lamina 110, (the bone that curves around and covers the spinal canal 108 as shown in FIG. 9), and any disk tissue causing pressure on a nerve or the spinal canal 108, are partially removed. This technique is highly invasive and traumatic to the body, and therefore requires an extended recovery time of about five weeks and a hospital stay of a few days. In addition to the trauma inflicted on the body from even a successful surgery, there are increased risks of future problems due to the removed portion of the lamina 110 which is no longer in place to support and protect the spinal canal 108 at the area where the surgery took place. Further, the vertebrae 100 may shift due to the lack of support in the structure. Thus, simply removing the disk and parts of the vertebral bone is a short-term, pain-relieving corrective action but not a long-term solution.

Diskectomy is a form of spinal surgery wherein part of an intervertebral disk is excised typically through open surgical techniques. Recently, less invasive techniques referred to as percutaneous diskectomy or microdiskectomy have been developed to reduce the surgical trauma to the patient. In microdiskectomy, a much smaller incision is made than in normal open surgeries. A small retractor, working channel or tube is inserted through the posterior muscles (not shown) to allow access to the damaged or herniated disk. Surgeons utilize special surgical instruments modified to work in such small openings such as curettes, osteotomes, reamers, probes, retractors, forceps, and the like to cut and remove part of the disk while monitoring their technique using a microscope, a fluoroscope (real-time X-ray monitoring), and/or an endoscope (a miniature TV camera with associated viewing monitor). While this technique is much less invasive than conventional open surgeries, due to their design the instruments presently available tend to extend the length of time of the surgery and may cause possible damage to areas other than the herniated disk.

A spinal fusion is a procedure that involves fusing together two or more vertebrae in the spine using bone grafts and sometimes using metal fixation with screws, plates or metal rods. The removal of a significant amount of disk material or numerous surgeries often increases the instability of the spine 120 thereby necessitating spinal fusion surgery. The fusion procedure is often used to correct kyphosis or scoliosis, in addition to those patients who require spine stabilization due to vertebral damage from ruptured disks, fractures, osteomyelitis, osteoarthritis or tumors, and the like. In a fusion procedure, a damaged disk may be completely removed. Parts of a bone from another part of the body, such as the pelvis, are harvested, and the bone parts or grafts are subsequently placed between the adjacent vertebrae 100 so that the adjacent vertebrae 100 grow together in a solid mass. In the fusion surgery, which is presently performed as an open surgical technique, the posterior lamina 110 and the centers of the vertebral bodies 106 may both be cut. The surgery often involves consequential damage to the associated posterior ligaments, muscles and joints in addition to the removal of part or all of the lamina 110.

In general, small pieces of bone are placed into the space between the vertebrae to be fused, but sometimes larger pieces of bone are used to provide immediate structural support. The source of the bone may be the patient, (autologous or autograft bone) or a bone bank harvested from other individuals, i.e. allograft bone. While autologous bone is generally considered better for promoting fusion between the vertebrae, it also necessitates extra surgery to remove bone from the patient's body. As with any surgery, risks can include bleeding, infection, adverse reactions to drugs, and difficulty under anesthesia. Additionally, the site of the bone graft harvest may cause pain in addition to the pain the patient is already suffering due to the difficulties associated with the vertebrae 100 or disk. Due to the nature of the conventional spinal fusion surgery, typically an open surgery wherein muscles and ligaments are cut and bone is chiseled away to allow access to the intervertebral space, recovery following fusion surgery is generally longer than any other type of spinal surgery. Patients typically stay in the hospital for three or four days or more and may require significantly greater time to return to normal activities since the surgeon normally requires evidence of bone healing. The recovery time for a normal spinal fusion surgery is significant due not only to the fact that normal movement cannot be allowed until detectable bone growth has occurred between the bone grafts and the adjacent vertebrae 100, but the associated ligaments, muscles and the location where the bone grafts were harvested must also recover. Oftentimes portions of the spine 120 must be immobilized during the recovery period causing added discomfort and inconvenience to the patient.

The concept of using a cage device for spinal fusion is not new. Several fusion cages are disclosed in U.S. Pat. Nos. 4,961,740, 5,702,449, 5,984,967, and 6,039,762, the subject matter of which is incorporated herein by reference.

One prior art fusion cage device, disclosed in U.S. Pat. No. 4,961,740 of Ray et al. (hereinafter "Ray"), is a large cylindrically shaped fusion cage that has a deep helical thread around the outer surface. In order to install the fusion cage of Ray, laminectomies must be performed on each side of the overlying lamina in order to provide access for the large cylindrically shaped fusion cage and if the disk space has narrowed as a result of degeneration, a scissors jack-type spreader or hydraulically inflated bladder is inserted on each side and opened to allow access to the disk space. A pilot cutter and pilot rod are used to cut female bone threads through the opposing vertebral endplates prior to threading the fusion basket into the now threaded interdiskal bore. Obviously the surgery is lengthy, highly intrusive and traumatic, and as noted in the Ray specification takes several weeks for recovery.

Other prior art devices, disclosed in U.S. Pat. Nos. 5,702, 449 and 6,039,762 of McKay (hereinafter, "McKay"), are cylindrically shaped spinal implants with perforations or apertures located through the outside walls. While the implants of McKay provide for a non-metal, bone graft substitute, they still require open surgical techniques for implantation due to their size and geometric shape.

Further, the concept of using an implant device for spinal support and stability is not new. Implants were used by Dr. Fernstrom in the 1960's including stainless steel spherical ball bearings (see "Spine Arthroplasty," *Spine Industry Analysis Series*, Viscogliosi Bros., LLC, November 2001).

What is needed, but not provided in the prior art, is a stand alone vertebral defect device that can be inserted into the intervertebral space with minor open surgery in a procedure utilizing minimally invasive techniques. Further, there is a need for such a vertebral defect device which can be used either to assist with fusion or can be used to maintain support and stability while preserving motion of the involved spine segment.

BRIEF SUMMARY OF THE INVENTION

Briefly stated, the present invention is directed to an insertion tool for a vertebral defect device having upper and lower openings. The insertion tool includes a first finger sized and shaped to cooperatively engage the upper opening and a second finger is sized and shaped to cooperatively engage the lower opening. An outer surface of each finger is shaped to match a contoured shape of the vertebral defect device proximate to the respective finger to allow a smooth insertion of the vertebral defect device between a pair of adjacent vertebrae. A driving member is sized and shaped to engage a body of the vertebral defect device, such that during insertion the driving member is driven to push the vertebral defect device between the pair of adjacent vertebrae.

In another aspect, the present invention is directed to a combination of a vertebral defect device and an insertion tool. The vertebral defect device includes a convexly tapered distal end, a proximal end, a top, a bottom, a first, a second side and an outer surface having generally rounded edges thereby facilitating insertion into an intervertebral space between a pair of adjacent vertebrae. The top has an upper opening and the bottom has a lower opening The insertion tool includes a first finger sized and shaped to cooperatively engage the upper opening and a second finger sized and shaped to cooperatively engage the lower opening. A driving member is sized and shaped to engage a body of the vertebral defect device. An outer surface of each finger is shaped to match a contoured shape of the vertebral defect device proximate to the respective finger to allow a smooth insertion of the vertebral defect device into the pair of adjacent vertebrae. During insertion the driving member is driven to push the vertebral defect device into the intervertebral space. The combination has generally smooth and rounded edges on exterior surfaces exposed during insertion into an intervertebral space.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Certain terminology is used in the following description for convenience only and is not limiting. The words "right", "left", "lower", and "upper" designate directions in the drawing to which reference is made. The words "inwardly" and "outwardly" refer direction toward and away from, respectively, the geometric center of the vertebral defect device and designated parts thereof. The terminology includes the words above specifically mentioned, derivatives thereof and words of similar import. Additionally, the word "a", as used in the claims and in the corresponding portions of the specification, means "at least one."

The term "vertebral defect device" as used herein may be applicable to a fusion cage device, a partial disk replacement device or a nuclear replacement device without departing from the present invention, and should be construed to broadly encompass any device for use in correcting defects in the spine.

Figure 1:
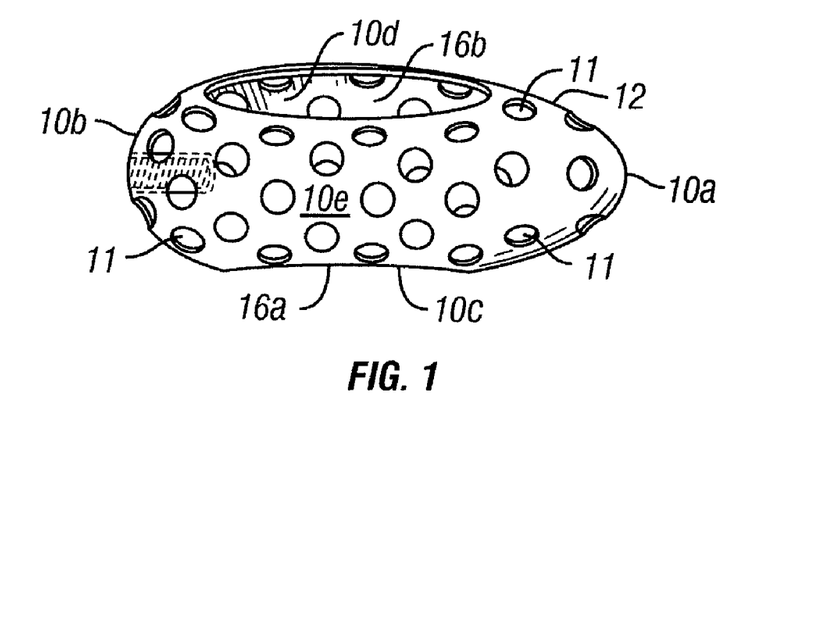
FIG. 1 is a perspective view of a first preferred embodiment of a vertebral defect device in accordance with the present invention.
Figure 2:
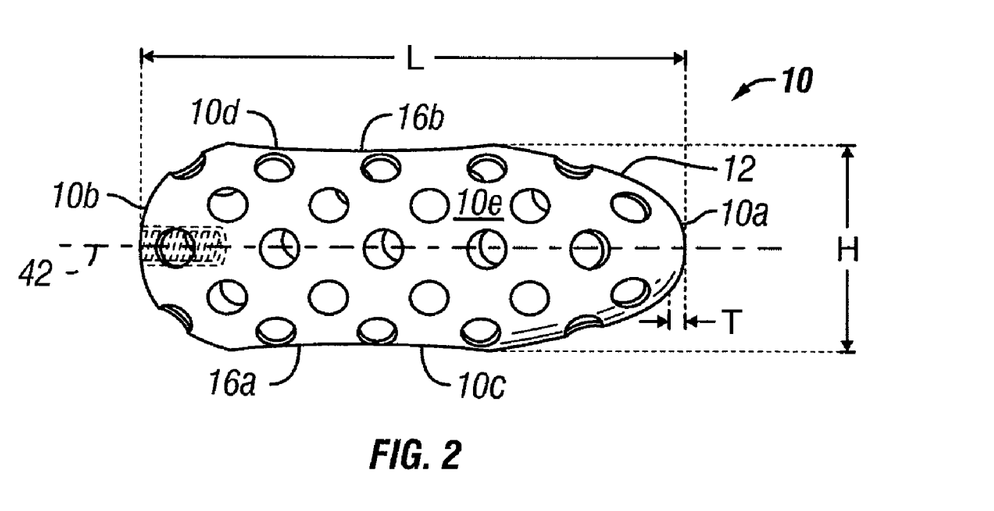
FIG. 2 is a side elevational view of the vertebral defect device of FIG. 1.
Figure 3:
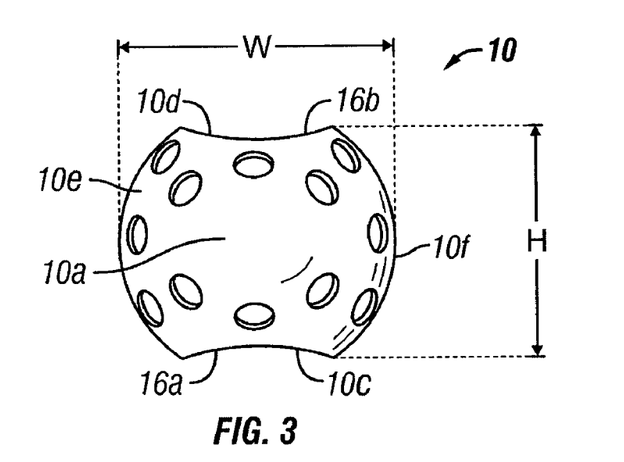
FIG. 3 is a front elevational view of the vertebral defect device of FIG. 1.
Figure 4:
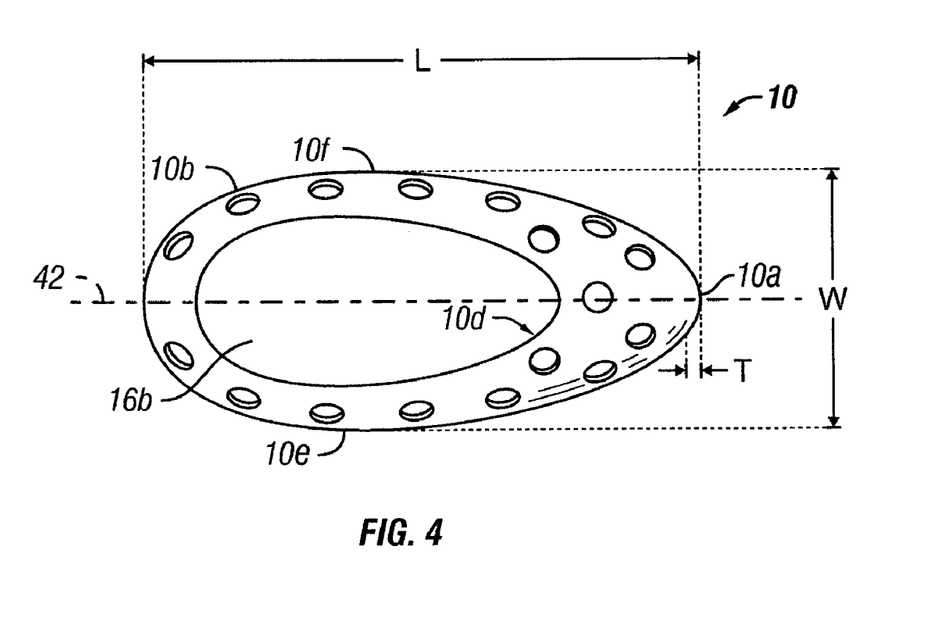
FIG. 4 is a top plan view of the vertebral defect device of FIG. 1.

Referring to the drawings in detail, wherein like reference numerals indicate like elements throughout, there is shown in FIG. 1 a vertebral defect device 10 in accordance with a first preferred embodiment of the present invention. The vertebral defect device 10 has a housing, a convexly-tapered distal end 10a, a convexly-tapered proximal end 10b, a lower wall 10c, an upper wall 10d, a first sidewall 10e, and a second sidewall 10f (FIGS. 3, 4). An outer surface 12 is substantially smooth over the entire surface. The vertebral defect device 10 may be titanium, or any metal or alloy compatible with MRI scanners, synthetic or polymeric materials, composites, ceramic, a biocompatible polymeric material, any biologically absorbable material and the like without departing from the broad inventive scope of the present invention.

The vertebral defect device 10 is generally lens-shaped or ovoid-shaped with rounded or contoured edges on all sides. In particular, the proximal end 10b preferably is rounded but more bluntly-shaped than the distal end 10a which preferably is sloped into a bullet-shaped tip. The proximal end 10b is preferably generally ovoid-shaped. Thus, the distal end 10a has a lesser average radius of curvature than the proximal end 10b. The lower wall 10c and upper wall 10d preferably are generally convex in order to cooperatively mate within the natural concavities of adjacent vertebral bodies 100. Similarly, the first sidewall 10e and second sidewall 10f of the vertebral defect device 10 preferably are similarly convex for similar reasons and to facilitate installation of the vertebral defect device 10 into an intervertebral space 121. The shape of the vertebral defect device 10 is ideally suited for insertion through a small opening, and therefore, the vertebral defect device 10 is well suited for minimally invasive and/or outpatient procedures.

Distributed evenly about the surface 12 of the vertebral defect device 10 are perforations or apertures 11. The apertures 11 are intended to promote rapid bone ingrowth while the vertebral defect device 10 maintains a stiff support structure between the vertebrae 100 during the growth process. While in the presently preferred embodiment, the apertures 11 are shown as circular in shape, the apertures 11 could be any shape including ovals, squares, rectangles, triangles, diamonds, crosses, X-shapes, and the like without departing from the spirit and scope of the invention. But, there need not be apertures 11. Preferably in the first preferred embodiment of the vertebral defect device, the lower wall 10c defines a lower opening 16a and the upper wall 10d of the vertebral defect device 10 defines an upper opening 16b at the point of vertebral contact to encourage successful fusion. The lower opening 16a and the upper opening 16b may be rectangular, circular, elliptical, or the like and may or may not be symmetrically-shaped. The openings 16a, 16b are preferably identically-shaped with respect to one another and are preferably symmetrically-shaped, but need not be. Further, the size of openings 16a and 16b may be varied to accommodate patient variations.

The length of the vertebral defect device as measured from the distal end 10a to the proximal end 10b preferably is approximately 10-30 mm, depending on the particular intervertebral space 121 in which the vertebral defect device 10 is to be inserted. For example, the intervertebral space between lumbar vertebra $L^{III}$ and lumbar vertebra $L^{IV}$ for an average male would accommodate a vertebral defect device 10 of a length between approximately 25-30 mm. But, the length of the vertebral defect device 10 could vary from the aforementioned range without departing from the spirit of the invention.

The width of the vertebral defect device 10 as measured between the first sidewall 10e and the second sidewall 10f of the vertebral defect device 10 will vary from approximately 10 mm to 25 mm depending upon the particular intervertebral space 121 in which the vertebral defect device 10 is to be inserted. For example, the intervertebral space between vertebra $L^{III}$ and vertebra $L^{IV}$ in an average male would accommodate a vertebral defect device 10 having a width of approximately 15-20 mm. But, the width of the vertebral defect device 10 could vary from the aforementioned range without departing from the spirit of the invention.

The height of the vertebral defect device 10 as measured between the upper wall 10d and the lower wall 10c of the vertebral defect device 10 will vary from approximately 5 mm to 25 mm depending upon the particular intervertebral space 121 in which the vertebral defect device 10 is to be inserted. For example, the intervertebral space between vertebra $L^{III}$ and vertebra $L^{IV}$ in an average male would accommodate a vertebral defect device 10 having a height of approximately 8-16 mm. But, the height of the vertebral defect device 10 could vary from the aforementioned range without departing from the spirit of the invention.

The overall shape of the vertebral defect device 10 is designed for insertion using minimally invasive techniques through a special portal or channel allowing a procedure to be implemented on an outpatient basis. Further, the vertebral defect device 10 is a self centering device because the shape of the vertebral defect device 10 will encourage it to settle within the natural concavities of adjacent vertebral bodies 100. As such, placement of the vertebral defect device 10 is much faster than that of prior art devices, thereby effectively reducing the duration of a procedure and the associated risks therewith. The smooth contour and edges of the vertebral defect device 10 provide for a safe and easy entrance into the intervertebral space 121.

The convex, bullet-like shape of the distal end 10a of the vertebral defect device 10 will allow it to be driven into the intervertebral space by merely temporarily distracting the vertebrae with minimal removal of the vertebral rim or annulus (not shown clearly) at the point of entry, thereby reducing the chance of dislodging the device post-surgery. Additionally, the self-centering feature of the vertebral defect device 10 will allow rapid settling of the vertebral defect device 10 into adjacent bone to promote rapid bone ingrowth while retention of most of the annulus and peripheral rim of the bodies (vertebrae) would provide good load sharing support to prevent excessive subsidence, where subsidence results from the natural settling of intervertebral matter into a softer central portion of the vertebral bodies 108.

Figure 7:
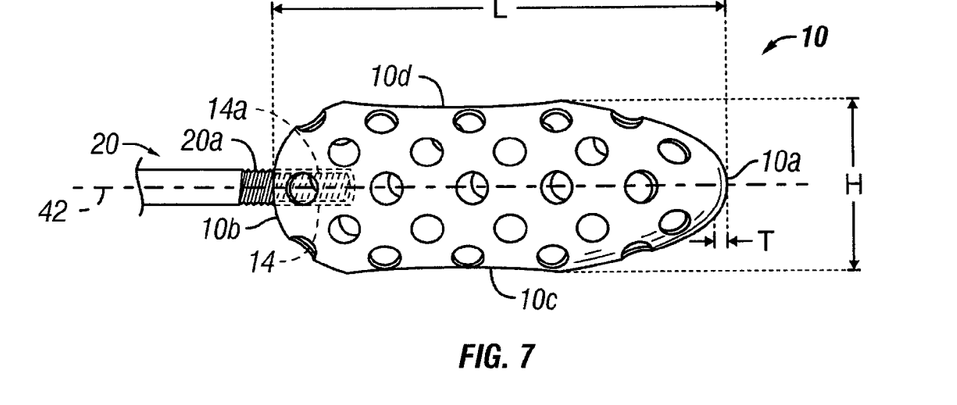
FIG. 7 is a side elevational view of the vertebral defect device of FIG. 1 connected to a first preferred embodiment of an insertion tool in accordance with present invention.

FIG. 7 shows the vertebral defect device 10 of the first preferred embodiment with a first preferred embodiment of a specially designed insertion tool 20. The insertion tool 20 is threaded into a socket 14 in the proximal end of the vertebral defect device 10. The socket 14 is provided with female threads 14a which are configured to accept the male threads 20a of the insertion tool 20. The insertion tool 20 may be formed of any substantially rigid material, but preferably is formed of a material that is bio-compatible such as titanium, stainless steel, nickel, or of a bio-compatible alloy, composite, polymeric material or the like. It should be noted that the material of construction of the insertion tool could be any material without diverging from the broad scope of the present invention. It is also contemplated that the insertion tool 20 and vertebral defect device 10 may be releasably coupled by any of several releasable fastening mechanisms known to those skilled in the art.

Figure 14A:
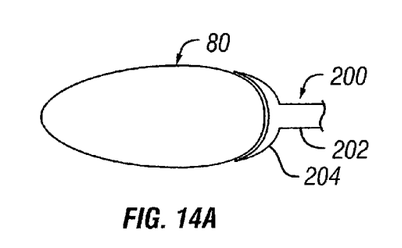
FIG. 14A is a side elevational view of a second preferred embodiment of an insertion tool for a vertebral defect device in accordance with the present invention.
Figure 14B:
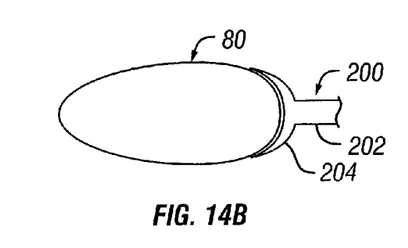
FIG. 14B is a top plan view of the insertion tool of FIG. 14A.

FIGS. 14A-14B show a second preferred embodiment of an insertion tool 200 for a vertebral defect device 10, 70, 80, 90, or 190 in accordance with the present invention. The insertion tool 200 has an elongate handle 202 and a grip 204. The grip 204 may be a suction cup or other similar gripping-type mechanism.

Figure 8:
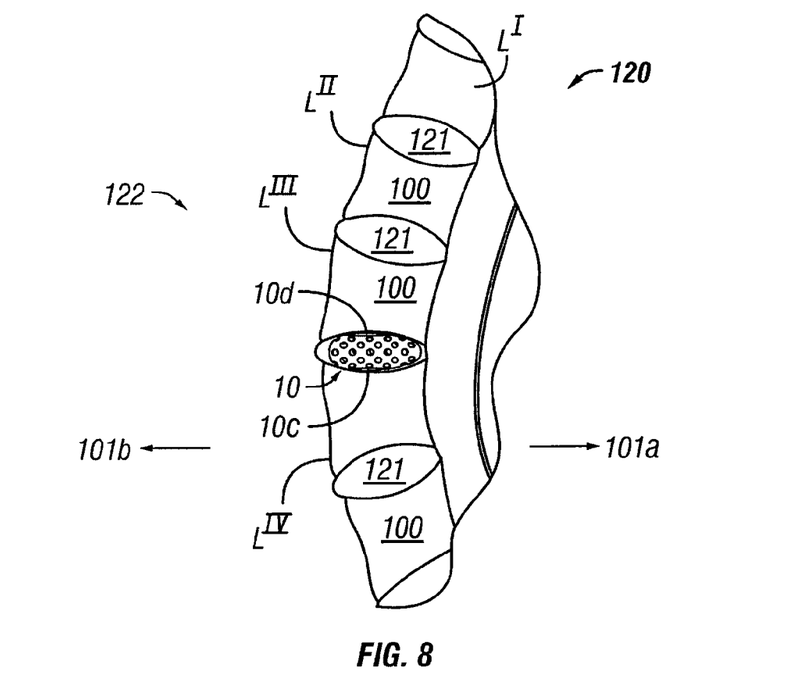
FIG. 8 is a side view of the vertebral defect device of FIG. 1 installed between lumbar vertebrae $L^{III}$ and $L^{IV}$.

FIG. 8 shows a side view of the lumbar region 122 of a portion of a human spine 120. In particular, a vertebral defect device 10 in accordance with the first preferred embodiment of the present invention is shown installed between lumbar vertebra $L^{III}$ and lumbar vertebra $L^{IV}$. In this particular installation, the second sidewall 10f of the vertebral defect device 10 is placed on the anterior side of the $L^{III}$-$L^{IV}$ intervertebral space, the first sidewall 10e of the vertebral defect device 10 is placed closest to the posterior side of the $L^{III}$-$L^{IV}$ intervertebral space, the upper wall 10d of the vertebral defect device 10 is adjacent to vertebra $L^{III}$, and the lower wall 10c of the vertebral defect device 10 is adjacent to vertebra $L^{IV}$. In this example, the surgeon would have inserted the distal end 10a of the vertebral defect device 10 into the gap between the $L^{III}$-$L^{IV}$ vertebrae as depicted in FIG. 9 by a directional arrow D. It is just as likely and possible for the surgeon to place the distal end 10a of the vertebral defect device 10 through the space between the $L^{III}$-$L^{IV}$ vertebrae in the direction of a directional arrow C (FIG. 9) or from other directions.

Figure 5:
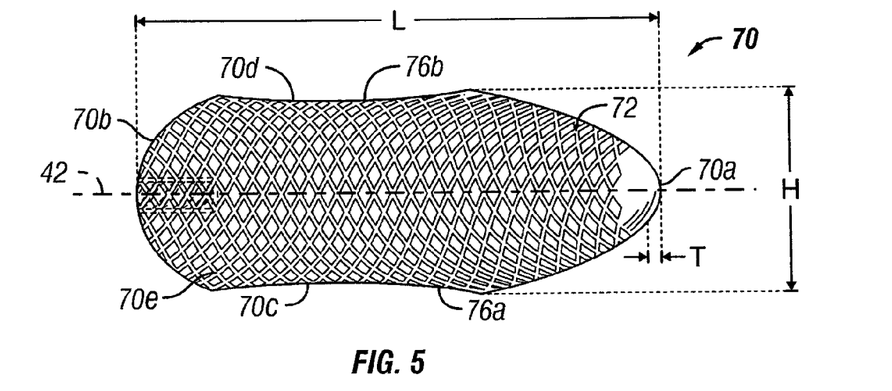
FIG. 5 is a side elevational view of a second preferred embodiment of a vertebral defect device in accordance with present invention.

FIG. 5 shows a side elevational view of a second preferred embodiment of a vertebral defect device 70 in accordance with the present invention. The intervertebral defect device or vertebral defect device 70 has a distal end 70a, a proximal end 70b, a lower wall 70c, an upper wall 70d, a first sidewall 70e, and a second sidewall (not shown). An outer surface 72 differs from the first preferred embodiment only in that the outer surface 72 of the vertebral defect device 70 is a lattice-type structure, instead of the body having a plurality of apertures 11, but the outer surface 72 is also substantially smooth with rounded edges and can be made from similar materials as described with reference to the first preferred embodiment. In an alternate embodiment of the second preferred embodiment of the vertebral defect device 70, the lower wall 70c defines a lower opening 76a and the upper wall 70d defines an upper opening 76b at the point of vertebral contact to encourage successful fusion.

Figure 6A:
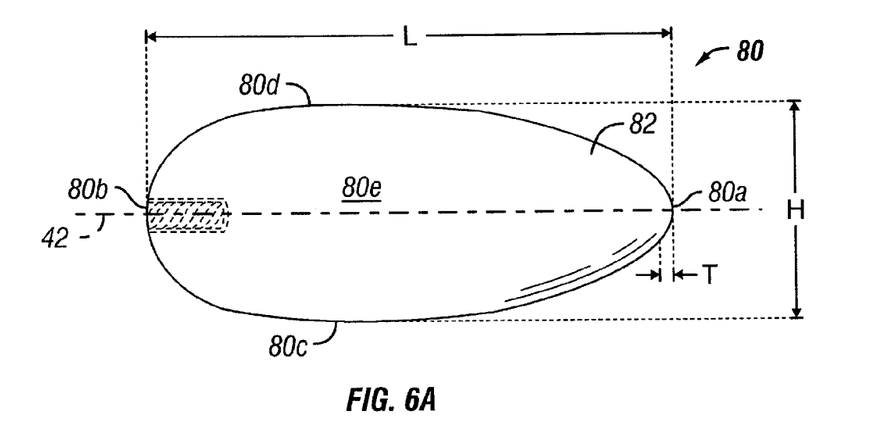
FIGS. 6A-6B are side elevational views of a third preferred embodiment of a vertebral defect device in accordance with present invention.
Figure 6B:
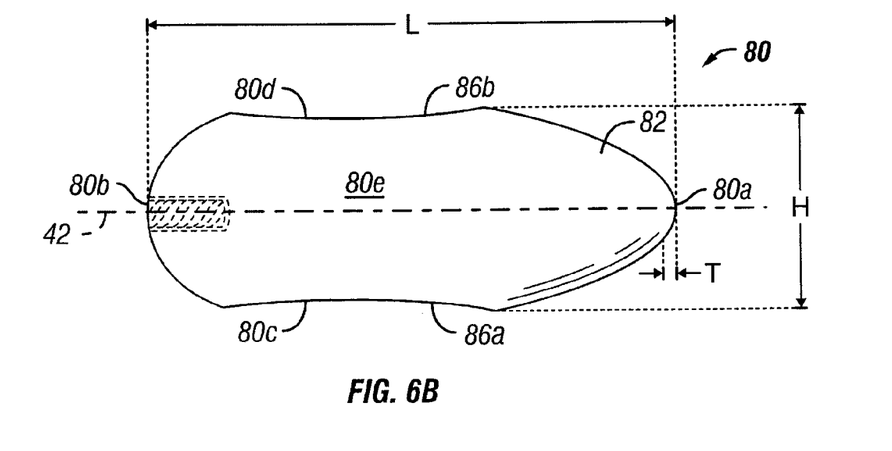

FIGS. 6A-6B show a third preferred embodiment of a vertebral defect device 80 in accordance with the present invention. FIG. 6A shows that the vertebral defect device 80 has a distal end 80a, a proximal end 80b, a lower wall 80c, an upper wall 80d, a first sidewall 80e, and a second sidewall (not shown). The vertebral defect device 80 further has an outer surface 82, which in the present embodiment, is substantially smooth and free from apertures, openings, and the like. The presently preferred embodiment is ideally suited for use as a disk prosthesis or nuclear replacement-type device due to the lack of openings. It would be obvious to one skilled in the art to form the vertebral defect device 80 out of a material that would not encourage adhesion or bone or tissue growth. Optionally, as shown in FIG. 6B, when the vertebral defect device 80 is applied as a fusion cage-type device, the lower wall 80c defines a lower opening 86a and the upper wall 80d defines an upper opening 86b for intervertebral contact to encourage successful fusion.

Figure 11:
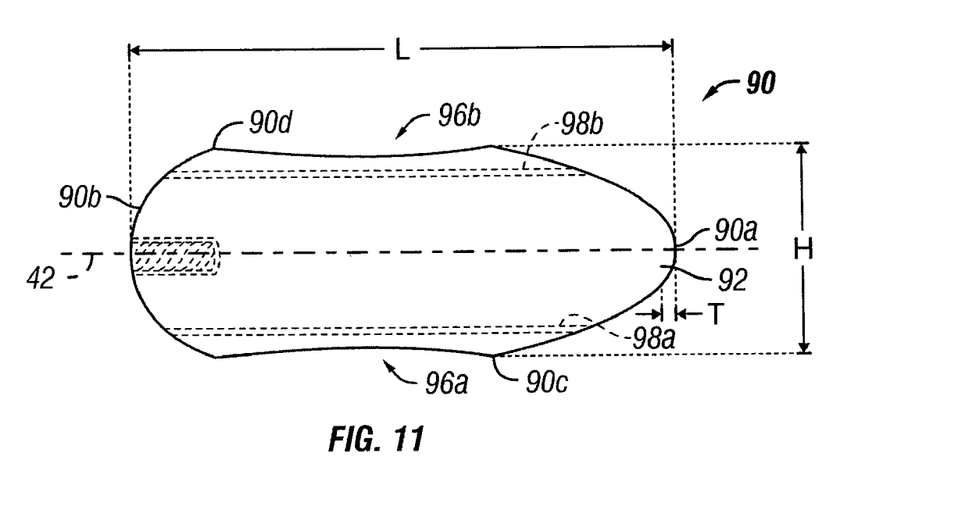
FIG. 11 is a side elevational view of a fourth preferred embodiment of a vertebral defect device in accordance with the present invention.
Figure 12:
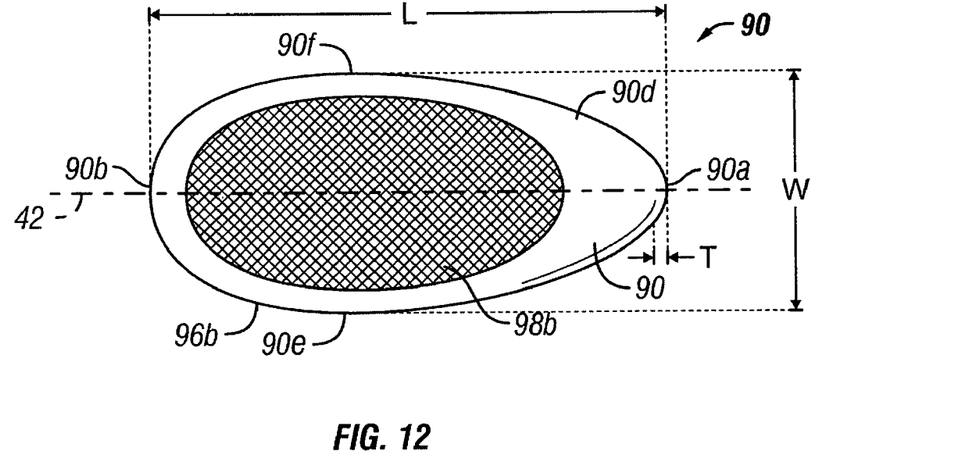
FIG. 12 is a top plan view of the vertebral defect device of FIG. 11.

FIGS. 11 and 12 show a fourth preferred embodiment of a vertebral defect device 90 in accordance with the present invention. The vertebral defect device 90 has a distal end 90a, a proximal end 90b, a lower wall 90c, an upper wall 90d, a first sidewall 90e, and a second sidewall 90f. The vertebral defect device 90 further has an outer surface 92, which in the present embodiment, is substantially smooth and free from apertures, openings, and the like, but may have apertures without departing from the present invention. The lower wall 90c defines a lower opening 96a and the upper wall 90d defines an upper opening 96b for intervertebral contact to encourage successful fusion. The vertebral defect device 90 further includes a lower grating 98a and an upper grating 98b. Preferably, the gratings 98a, 98b are formed of a substantially rigid mesh that is coated with a bio-compatible ceramic to promote bone growth. The gratings 98a, 98b are located slightly below an outer edge defined by the openings 96a, 96b in order to allow some or partial subsidence of the vertebrae 100 partially into the vertebral defect device 90, but will prevent excessive subsidence. It has been contemplated that in lieu of openings 96a, 96b, the gratings 98a, 98b are merely recessed portions of the lower wall 90c and upper wall 90d having perforations, apertures or slits which allow bone ingrowth.

Figure 13A:
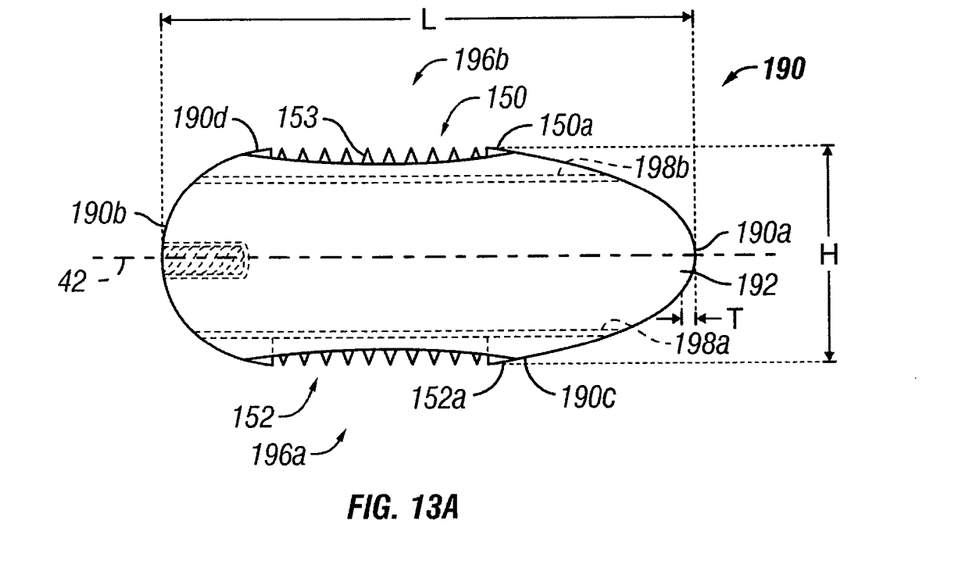
FIG. 13A is a side elevational view of a fifth preferred embodiment of a vertebral defect device in accordance with the present invention.
Figure 13B:
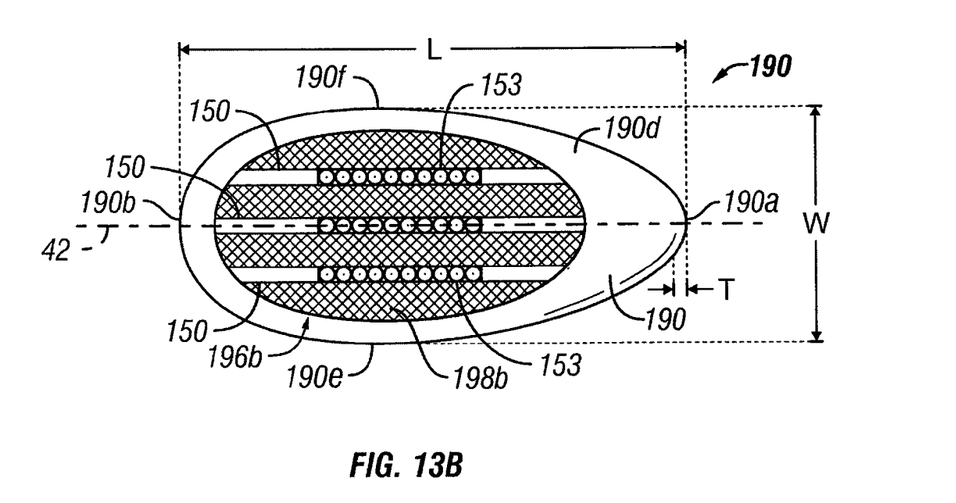
FIG. 13B is a top plan view of the vertebral defect device of FIG. 13A.

FIGS. 13A and 13B show a fifth preferred embodiment of a vertebral defect device 190 in accordance with the present invention. The vertebral defect device 190 has a distal end 190a, a proximal end 190b, a lower wall 190c, an upper wall 190d, a first sidewall 190e, and a second sidewall 190f. The vertebral defect device 190 further has an outer surface 192, which in the present embodiment, is substantially smooth and free from apertures, openings, and the like, but may have apertures without departing from the present invention. The lower wall 190c defines a lower opening 196a and the upper wall 190d defines an upper opening 196b for intervertebral contact to encourage successful fusion. The vertebral defect device 190 further includes a lower grating 198a and an upper grating 198b. Preferably, the gratings 198a, 198b are formed of a substantially rigid mesh that is coated with a bio-compatible ceramic to promote bone growth. The gratings 198a, 198b are located slightly below an outer edge defined by the openings 196a, 196b in order to allow some subsidence of the vertebrae 100 partially into the vertebral defect device 190, but will prevent excessive subsidence.

Further, the vertebral defect device 190 includes at least one upper arch 150 and at least one lower arch 152, but preferably the vertebral defect device 190 includes three upper arches 150 and three lower arches 152. The arches 150, 152 are generally disposed symmetrically along and about a centerline of the longer axis of the vertebral defect device 190 and are secured to the body of the vertebral defect device 190. Of course the arches 150, 152 may be secured to the vertebral defect device 190 by other means and may be disposed in other orientations without departing from the spirit of the present invention. Preferably, the arches 150, 152 protrude above the top and bottom 190d, 190c of the vertebral defect device 190, respectively. The arches 150, 152 are configured to settle into bone matter, and therefore, the arches 150, 152 have sharpened edges 150a, 152a. The sharpened edges 150a, 152a may include serrations, pins, sharpened cones or a simple knife-like edge, but need not be. Preferably, the sharpened edges 150a, 152a are partially knife like proximate the ends of the arches and partially covered with sharpened cones 153. The arches 150, 152 are preferably about 0.5 mm to about 2.0 mm wide. The arches 150, 152 also serve to center the vertebral defect device 190 during placement and prevent the vertebral defect device from rolling or canting thereafter.

It should be obvious to one skilled in the art that arches 150, 152 could be utilized in any of the embodiments of the vertebral defect devices 10, 70, 80, 90, or 190, as described herein.

Figure 15A:
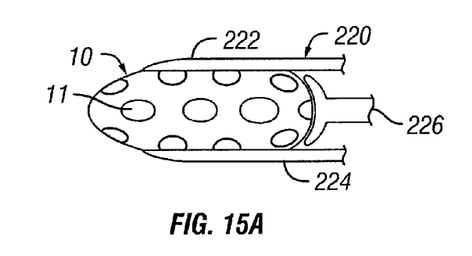
FIG. 15A is a side elevational view of a third preferred embodiment of an insertion tool for a vertebral defect device in accordance with the present invention.
Figure 15B:
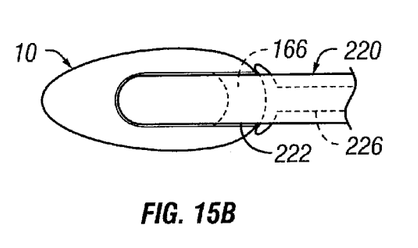
FIG. 15B is a top plan view of the insertion tool of FIG. 15A.

FIGS. 15A-15B show a third preferred embodiment of an insertion tool 220 for a vertebral defect device 10 (70, 80, or 90) having upper and lower openings 16a, 16b (76a, 76b, 86a, 86b, 96a, 96b). The insertion tool 220 has a first finger 222 configured to cooperatively engage the upper opening 16a and a second finger 224 configured to cooperatively engage the lower opening 16b. The fingers 222, 224 have outer surfaces which are shaped to match the contoured shape of the vertebral defect device 10 to allow a smooth insertion of the vertebral defect device 10. The combination of the insertion tool 220 and the vertebral defect device 10 when the first and second fingers 222, 224 are engaged with the ingrowth openings 16a, 16b, forms a combined structure having generally rounded exposed surfaces. The fingers 222, 224 also prevent foreign matter and debris from getting caught in the openings 16a, 16b during insertion. Because the fingers 222, 224 grasp the vertebral defect device 10 in a specific orientation defined by the upper and lower openings 16a, 16b, the insertion tool 220 provides the surgeon with means to orient the vertebral defect device 10 correctly during insertion.

The insertion tool 220 further includes a driving member 226 that is configured to engage the body of the vertebral defect device 10. The driving member 226 is configured to be impacted such that during insertion a surgeon may tap or hammer the driving member 226 to push the vertebral defect device 10 through a small opening. Preferably, the first and second fingers 222, 224 are retractable relative to the driving member 226. Thus, after the defect device 10 is inserted to a desired position, the first and second fingers 222, 224 are retracted while the driving member 226 holds the defect device 10 in place. Optionally, the vertebral defect device 10 may have grooves 166 (shown in phantom in FIG. 15B) extending from the upper and lower openings 16a, 16b to facilitate the removal of the retractable fingers 222, 224.

Figure 16A:
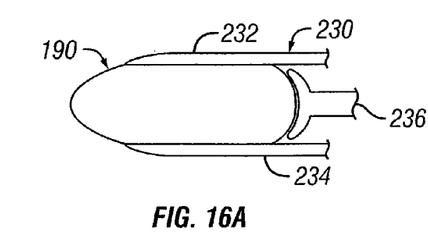
FIG. 16A is a side elevational view of a fourth preferred embodiment of an insertion tool for a vertebral defect device in accordance with the present invention.
Figure 16B:
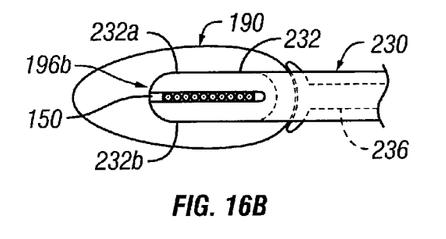
FIG. 16B is a top plan view of the insertion tool of FIG. 16A.

FIGS. 16A-16B is a side elevational view of a fourth preferred embodiment of an insertion tool 230 for a vertebral defect device 190 having upper and lower openings 196a, 196b and upper and lower arches 150, 152. For example, the upper finger 232 has first and second prongs 232a, 232b for straddling the upper arch 150 as best seen in FIG. 16B. The insertion tool 230 is similar to the insertion tool 220, but each of the retractable fingers 232 234 is forked to accommodate the arches 150, 152. Preferably, the arches 150, 152 are just below the outer surface of the fingers 232, 234, so that the arches 150, 152 do not injure adjacent tissue during insertion. Furthermore, it would be obvious to one skilled in the art to utilize multiple prongs 232a, 232b in each of the retractable fingers 232, 234 in order to accommodate multiple arches 150, 152.

The vertebral defect device 10 has a maximum height H and/or maximum width W, preferably in the range of 6 to 15 mm, at an axial location intermediate the distal end 10a and the proximal end 10b. The vertebral defect device 10 has a length L, preferably in the range of 10 to 30 mm, along a longitudinal axis 42. An outer profile of the vertebral defect device 10 is characterized by a relatively gradual slope, such that the diameter (height and width) of the vertebral defect device 10 preferably changes no more than about 2 mm for every 1 mm change in length. Preferably, the distal end 10a, in particular, has a slope that changes by no more than about 2 mm for every 1 mm change in length. The distal end 10a is preferably relatively small, for example, less than 2.5 mm in diameter over the terminal 1 mm T of the distal end 10a along the longitudinal axis 42 or approximately 5-20% of the maximum height H and/or maximum width W of the vertebral defect device 10. However, the distal end 10a should not be so pointed such that it would easily drive through or penetrate the opposite side of the annulus on the opposite side of the disk space. The taper and slope of the distal end 10a of the vertebral defect device 10 permit the vertebral defect device 10 to be at least partially self-distracting. Generally, the vertebral defect device 10 is intended to be impacted into the disk space while providing such distraction of the periphery of the vertebral bodies 100 to permit entry into nuclear center of the disk. The vertebral defect device 10 may be dimensioned in accordance with the requirements of specific applications, and other dimensional characteristics of the vertebral defect device 10 are included within the scope of this invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A combination comprising:
    a vertebral defect device comprising a housing having a convexly tapered generally bluntly rounded distal end, a proximal end, a top, a bottom, a first side, a second side and an outer surface having generally rounded edges thereby facilitating insertion into an intervertebral disk space between a pair of adjacent vertebrae, the top having an upper opening and the bottom having a lower opening, a length of the vertebral defect device as measured from the distal end to the proximal end being greater than a width of the vertebral defect device as measured between the first and second sides and being greater than a height of the vertebral defect device as measured between the top and bottom, a maximum width of the vertebral defect device as measured between the first and second sides being different than a maximum height of the vertebral defect device as measured between the top and bottom; and
    an insertion tool having a first finger sized and shaped to cooperatively engage the upper opening, a second finger sized and shaped to cooperatively engage the lower opening, and a driving member disposed between the first and second fingers and sized and shaped to engage at least a portion of an outer surface of said housing of the vertebral defect device, the first and second fingers being retractable with respect to the housing of the vertebral defect device, wherein an outer surface of each finger is shaped to match a contoured shape of the vertebral defect device proximate to the respective finger to allow a smooth insertion of the vertebral defect device between the pair of adjacent vertebrae and wherein during insertion the driving member is driven to push the vertebral defect device into an intervertebral disk space between the pair of adjacent vertebrae,
    wherein the vertebral defect device is generally egg-shaped with rounded or contoured edges on all exposed surfaces when the vertebral defect device is attached to the insertion tool, with the taper of the distal end diminishing more gradually than a taper of the proximal end,
    wherein the combination has generally smooth and rounded edges on exterior surfaces exposed during insertion into an intervertebral space.

2. The combination according to claim 1, wherein the first and second fingers are retractable, such that after the vertebral defect device is inserted to a desired position in the intervertebral disk space, the first and second fingers are retracted while the vertebral defect device is held in place by the driving member.

3. The combination according to claim 1, wherein the vertebral defect device includes at least one upper arch and at least one lower arch, and wherein the first finger has first and second prongs for straddling one of the upper and lower arches of the vertebral defect device.

4. The combination according to claim 1, wherein each of the first and second fingers are forked to accommodate the upper and lower arches of the vertebral defect device.

5. The combination according to claim 1, wherein the top and bottom of the vertebral defect device are at least partially convexly shaped enough to cooperatively mate with concavities of adjacent vertebrae, and the first and second sides are at least partially convexly shaped.

6. The combination according to claim 1, wherein the distal end of the vertebral defect device has a lesser average radius of curvature than the proximal end.

* * * * *